(12) United States Patent
Feingersch

(10) Patent No.: US 12,410,471 B2
(45) Date of Patent: Sep. 9, 2025

(54) DNA CONSTRUCT FOR SEQUENCING AND METHOD FOR PREPARING THE SAME

(71) Applicant: FORESEE GENOMICS LTD, Haifa (IL)

(72) Inventor: Roi Feingersch, Regba (IL)

(73) Assignee: Foresee Genomics Ltd., Haifa (IL)

( * ) Notice: Subject to any disclaimer, the term of this patent is extended or adjusted under 35 U.S.C. 154(b) by 502 days.

(21) Appl. No.: 17/828,686

(22) Filed: May 31, 2022

(65) Prior Publication Data

US 2023/0026055 A1 Jan. 26, 2023

Related U.S. Application Data

(63) Continuation of application No. 16/613,575, filed as application No. PCT/IL2018/050522 on May 14, 2018.

(60) Provisional application No. 62/505,920, filed on May 14, 2017.

(51) Int. Cl.
| | |
|---|---|
| *C12Q 1/68* | (2018.01) |
| *C12P 19/34* | (2006.01) |
| *C12Q 1/6806* | (2018.01) |
| *C12Q 1/6809* | (2018.01) |
| *C12Q 1/6827* | (2018.01) |
| *C12Q 1/6869* | (2018.01) |

(52) U.S. Cl.
CPC ......... *C12Q 1/6869* (2013.01); *C12Q 1/6806* (2013.01); *C12Q 1/6809* (2013.01); *C12Q 1/6827* (2013.01)

(58) Field of Classification Search
CPC .................................................. C12Q 1/6869
See application file for complete search history.

(56) References Cited

U.S. PATENT DOCUMENTS

| | | |
|---|---|---|
| 2013/0137587 A1 | 5/2013 | Van Eijk et al. |
| 2015/0148239 A1 | 5/2015 | Peter et al. |
| 2016/0253584 A1 | 9/2016 | Fodor et al. |
| 2016/0289740 A1 | 10/2016 | Fu et al. |
| 2017/0088832 A1 | 3/2017 | McEwan et al. |
| 2017/0114390 A1 | 4/2017 | Hindson et al. |
| 2020/0010875 A1* | 1/2020 | Mok ....................... C40B 40/06 |
| 2021/0395813 A1* | 12/2021 | Feingersch .......... C12Q 1/6806 |

FOREIGN PATENT DOCUMENTS

| | | |
|---|---|---|
| EP | 3635107 A1 | 4/2020 |
| WO | 2012142213 A2 | 10/2012 |
| WO | 2013096802 A1 | 6/2013 |
| WO | 2015083004 A1 | 6/2015 |
| WO | 2016077313 A1 | 5/2016 |
| WO | 2016176091 A1 | 11/2016 |
| WO | 2018211497 A1 | 11/2018 |

OTHER PUBLICATIONS

Schlecht et al., ConcatSeq: A method for increasing throughput of single molecule sequencing by concatenating short DNA fragments, Scientific Reports, 2017, https://www.researchgate.net/publication/318405698_ConcatSeq_A_method_for_increasing_throughput_of_single_molecule_sequencing_by_concatenating_short_DNA_fragments_OPEN.
U.S. Appl. No. 17/293,085; Response to OA of Jul. 5, 2024, dated Dec. 5, 2024.
U.S. Appl. No. 17/293,085; Interview Summary, dated Nov. 19, 2024.
U.S. Appl. No. 17/293,085; Office Action, dated Jul. 5, 2024.
EP application No. 18802131.5; communication dated Mar. 21, 2024.
EP application No. 18802131.5; response to European Search Report, dated Jul. 29, 2021.
EP application No. 18802131.5; European Search Report and Opinion, dated Dec. 14, 2020.
PCT application No. PCT/IL2018/050522; International Preliminary Report on Patentability, dated Nov. 19, 2019.
PCT application No. PCT/IL2018/050522; International Search Report, dated Aug. 14, 2018.

\* cited by examiner

*Primary Examiner* — Kenneth R Horlick
(74) *Attorney, Agent, or Firm* — William H. Dippert; Laurence A. Greenberg; Werner H. Stemer

(57) ABSTRACT

A DNA construct comprises multiple units sequentially attached one to the other, wherein a unit comprises: a segment; an index attached to one end of the segment; an identifier attached to another end of the segment; an introducer attached to a 5'-end of either the index or the identifier; and a closure attached to a 5'-end of a remaining either identifier or index. A method for preparing the DNA construct and a method for analyzing a sequence of the DNA construct, as well as various embodiments thereof, are disclosed herein.

11 Claims, 2 Drawing Sheets
Specification includes a Sequence Listing.

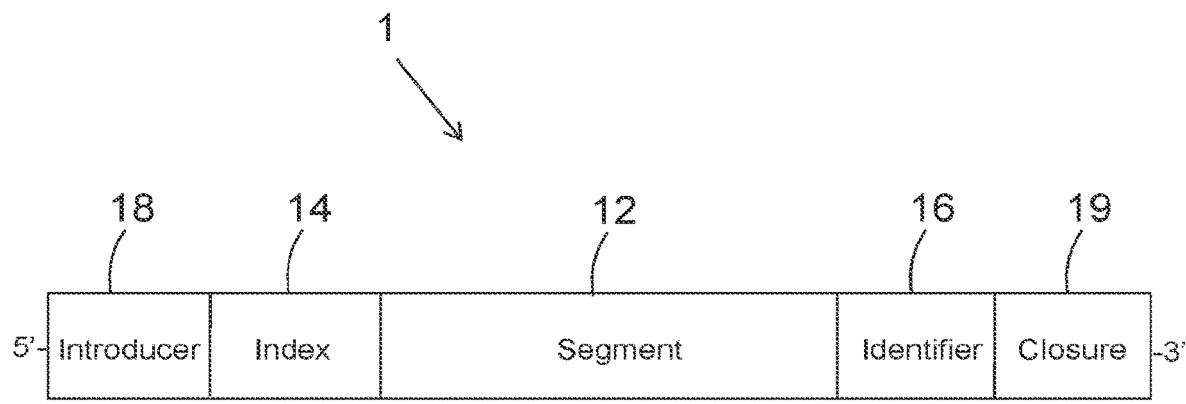
FIG. 1-A
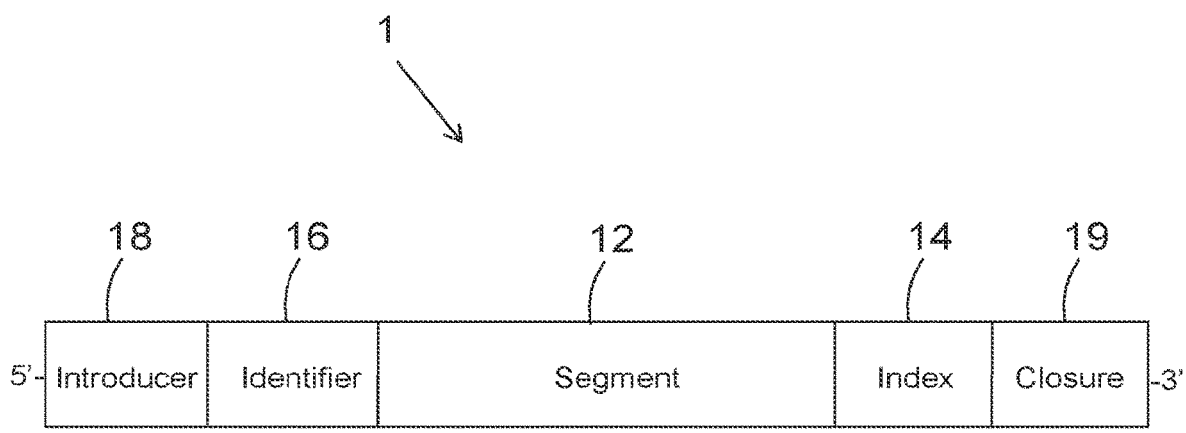
FIG. 1-B

DNA CONSTRUCT FOR SEQUENCING AND METHOD FOR PREPARING THE SAME

SEQUENCE LISTING

The instant patent application contains a Sequence Listing which has been submitted in ASCII format via EFS-Web and is hereby incorporated herein by reference in its entirety.

FIELD OF THE INVENTION

The present subject matter relates to DNA sequencing. More particularly, the present subject matter relates to the preparation of DNA for sequencing.

BACKGROUND OF THE INVENTION

Analysis of DNA sequences of patients enables better diagnostics and with that the ability to provide specific and better treatments for genetically-based ailments. A DNA sequence of a whole genome or target regions of an individual may be compared to known sequences of the human genome in order to find variations that account for potential diseases, for example mutations that may cause cancer. Knowing and understanding the genetic information of each patient with respect to specific ailments help in preventing adverse events, allow for providing appropriate drug treatments and promote maximal efficacy with drug prescriptions.

The field of DNA sequencing has been rapidly advanced during the last years, enabling relatively rapid sequencing of very long DNA fragments, in the range of thousands and even more than substantially 100,000 bp. For example, nanopore sequencing is an advanced DNA sequencing method that provides a short, easy and fast procedure of sequencing libraries of very long DNA segments. This technology has the potential to offer relatively low-cost genotyping, high mobility for testing, and rapid processing of samples with the ability to display results in real-time. An exemplary nanopore sequencing platform is MinIon (Oxford Nanopore Technology Limited, UK).

Nanopore sequencing is configured to sequence very long DNA fragments, in the range of substantially 1,000-10,000 base pairs (bp) and even more than substantially 100,000 bp. However, one drawback of nanopore sequencing is accuracy—substantially 90% accuracy. This is critical in diagnosing mutation-based diseases since there is no way to distinguish between mutations in the target sequence and errors in the sequencing that may be interpreted as mutations in the target sequence. In addition, one of the ways to prepare DNA for nanopore sequencing is amplifying a region of interest (ROI) by polymerase chain reaction (PCR). It is well known in the art that during PCR errors in the sequence of the PCR product are introduced due to poor proofreading by the DNA polymerase used in the PCR. These errors may also be interpreted as mutations in the target sequence. Furthermore, target DNA fragments that are normally sequenced for example for genotyping and diagnostics, are relatively much shorter—in the range of a few hundred base pairs, compared to thousands of base pair sequenced by nanopore sequencing. This renders nanopore sequencing not suitable for sequencing short DNA fragments.

SUMMARY OF THE INVENTION

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

According to one aspect of the present subject matter, there is provided a DNA construct comprising multiple units sequentially attached one to the other, wherein a unit comprises:
  a segment;
  an index attached to one end of the segment;
  an identifier attached to another end of the segment;
  an introducer attached to a 5'-end of either the index or the identifier, and
  a closure attached to a 3'-end of a remaining either identifier or index.

According to one embodiment, the length of the DNA construct is at least substantially 1,000 bp.

According to another embodiment, the length of the segment is up to substantially 1,000 bp.

According to yet another embodiment, the length of the segment is in the range of substantially 100-500 bp.

According to another aspect of the present subject matter, there is provided a method for preparing a DNA construct, the method comprising:
  obtaining a segment;
  attaching an index, an identifier, an introducer and a closure to the segment,
  wherein
  the index 14 attached to one end of the segment;
  the identifier is attached to another end of the segment;
  the introducer 18 is attached to a 5'-end either the index or the identifier; and
  the closure is attached to a 3'-end of a remaining either identifier 16 or index 14,
  giving rise to a pre-mature unit 1;
  amplifying the pre-mature unit with primers specific to the introducer and closure,
  giving rise to a double stranded mature unit 1;
  phosphorylating 5'-ends of the strands of the mature unit 1, and
  sequentially attaching mature units.

According to yet another aspect of the present subject matter, there is provided a method for analyzing a sequence of a DNA construct according to claim 1, the method comprising:
  separating sequences of units one from the other;
  grouping units having the same index for obtaining same index groups;
  grouping units having the same segment sequence in each same index group for obtaining same segment groups;
  grouping units having the same identifier sequence in each same segment group for obtaining same identifier 16 groups;
  collapsing multiple segment sequences in each same identifier group to a single sequence that accurately represents the sequence of the target sequence according to which the segment was obtained.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings:

FIGS. 1A-B schematically illustrate, according to some exemplary embodiments, a unit of a DNA construct.

DESCRIPTION OF THE PREFERRED EMBODIMENTS

Figure 2A:
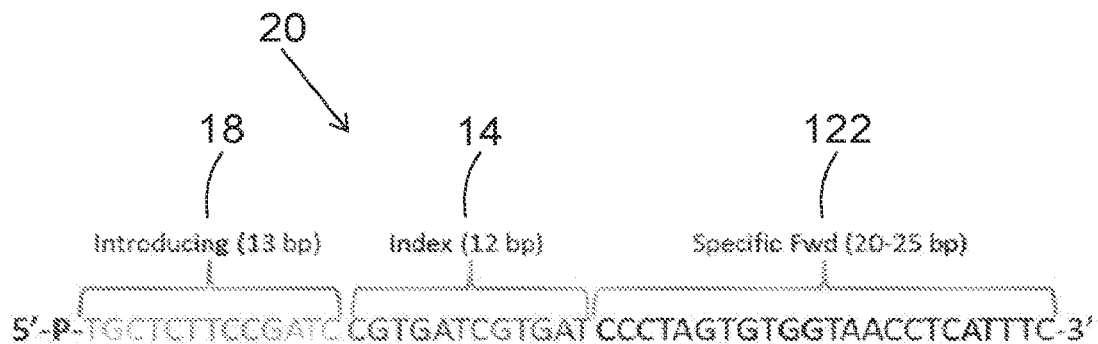
FIGS. 2A-B schematically illustrate, according to an exemplary embodiment, a forward primer and a reverse primer, respectively, for a first PCR.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

The present subject matter provides a DNA construct that allows sequencing of short DNA segments, for example in a length of hundreds base pairs, by platforms configured to sequence long DNA fragments, in the range of substantially 1,000-10,000 bp, and even up to 100,000 bp and more, for example the nanopore sequencing platform.

The present subject matter further provides a DNA construct that allows sequencing of short DNA segments, for example in a length of hundreds base pairs, multiple times, giving rise to accurate sequencing results, by platforms configured to sequence long DNA fragments, in the range of substantially 1,000-10,000 bp, and even up to 100,000 bp and more, for example the nanopore sequencing platform.

The present subject matter further provides a DNA construct that allows simultaneous sequencing of multiple different short DNA segments, for example in a length of hundreds base pairs, from different origins, by platforms configured to sequence long DNA fragments, in the range of substantially 1,000-10,000 bp, and even up to 100,000 bp and more, for example the nanopore sequencing platform, while allowing to identify each segment and its origin according to the sequences obtained.

The present subject matter additionally provides a DNA construct that allows distinguishing between mutations in a target sequence and errors introduced into the sequence obtained, for example by poor accuracy of the sequencing method and errors introduced during amplification of the ROI.

The present subject matter additionally provides a method for preparing a DNA construct that allows sequencing of short DNA segments, for example in a length of hundreds base pairs, by platforms configured to sequence long DNA fragments, in the range of substantially 1,000-10,000 bp, and even up to 100,000 bp and more, for example the nanopore sequencing platform.

The present subject matter further provides a method for preparing a DNA construct that allows sequencing of short DNA segments, for example in a length of hundreds base pairs, multiple times, giving rise to accurate sequencing results, by platforms configured to sequence long DNA fragments, in the range of substantially 1,000-10,000 bp, and even up to 100,000 bp and more, for example the nanopore sequencing platform.

The present subject matter additionally provides a method for preparing a DNA construct that allows simultaneous sequencing of multiple different short DNA segments, for example in a length of hundreds base pairs, from different origins, by platforms configured to sequence long DNA fragments, in the range of substantially 1,000-10,000 bp, and even up to 100,000 bp and more, for example the nanopore sequencing platform, while allowing to identify each segment and its origin according to the sequences obtained.

The present subject matter further provides a method for preparing a DNA construct that allows distinguishing between mutations in a target sequence and errors introduced into the sequence obtained, for example by poor accuracy of the sequencing method and errors introduced during amplification of the ROI.

The present subject matter further provides a method for analyzing DNA sequences obtained by sequencing of long DNA fragments, for example nanopore sequencing, while distinguishing between mutations in a target sequence and errors introduced into the sequence by the method itself, for example errors in sequencing and errors introduced during amplification of the ROI.

The DNA construct of the present subject matter dramatically improves the accuracy of DNA sequencing reads when sequencing short DNA segments, for example in a length of hundreds base pairs, by platforms configured to sequence long DNA fragments, in the range of substantially 1,000-10,000 bp, and even up to 100,000 bp and more, for example the nanopore sequencing platform. This DNA construct, then, may be used in diagnosing genetic variations with high sensitivity and specificity.

The DNA construct comprises a plurality of units.

FIGS. 1A-B schematically illustrate, according to some exemplary embodiments, a unit of a DNA construct. The unit 1 comprises a segment 12, namely a target DNA sequence, the analysis of which is desired. Any target DNA sequence known in the art is under the scope of the present subject matter, for example a gene or a part of a gene in which a mutation is sought for the diagnostics of a gene-based disease, like cancer, genetic disorder and the like. The segment 12 may be in any desire length. According to one embodiment, the segment is a few hundreds base pairs long, up to substantially 1,000 bp long. According to a preferred embodiment, the length of the segment 12 is in the range of substantially 100-500 bp.

The unit 1 further comprise an index 14 attached to one end of the segment 12 and an identifier 16 attached to an opposite side of the segment 12. As can be seen in FIG. 1A, according to one embodiment, the index 14 is attached to the 5'-end of the segment 12 and the identifier 16 is attached to the 3'-end of the segment 12. As can be seen in FIG. 1-B, according to another embodiment, the index 14 is attached to the 3'-end of the segment 12 and the identifier 16 is attached to the 5'-end of the segment.

According to one embodiment, the index 14 is a DNA sequence that is unique to the origin of the segment 12. A different index 14 sequence is attached to any copy of the segment 12 that originates from a certain origin. An origin may be for example an individual from which the segment 12 is obtained. Thus, the index 14 is configured to tag the origin of the segment 12. According to another embodiment, the index 14 is a DNA sequence that is unique for the target sequence of the segment 12. A different index 14 sequence is attached to any copy of the segment 12 that originates from a certain target sequence. A target sequence may be for example a certain gene that is diagnosed for mutations, a certain tag sequence and the like. A person skilled in the art should understand, then, that the index 14 may be simultaneously unique to the origin and the target sequence of the segment 12. The length of the index 14 may be any length that allows unique tagging of each origin. For example, the length of the index 14 is substantially 12 bp. It should be noted though that this is only an exemplary length and the any length of the index 14 is under the scope of the present subject matter.

According to one embodiment, the index 14 may be split to two parts and each part of the index 14 may be attached to any one of the two ends of the segment 12. For example, a 12 bp long index 14 is split to a first 6 bp index 14 part and a second 6 bp index 14 part. The first index 14 part is attached to one end of the segment 12 and the second index 14 part is attached to another end of the segment 12.

According to one embodiment, the identifier 16 is a DNA sequence that is unique for every copy of the segment 12. A different identifier 16 sequence is attached to each copy of the segment 12. Thus, the identifier 16 is configured to tag each copy of the segment 12. In a method described hereinafter, the unit 1 is amplified, for example by PCR and at a later stage the sequences of multiple copies of the unit 1 are analyzed. The sequences of the segments 12 of the units 1 that comprise the same identifier 16 are considered to be amplified from the same original segment 12, or original target sequence. Thus, as will be discussed hereinafter, one can distinguish between mutations in the original segment 12, or the original target sequence and errors introduced during the procedure. The length of the identifier 16 may be any length that allows unique tagging of each copy of the segment 12. For example, the length of the identifier 16 is substantially 12 bp. It should be noted though that this is only an exemplary length and the any length of the identifier 16 is under the scope of the present subject matter.

According to one embodiment, the identifier 16 may be split to two parts and each part of the identifier 16 may be attached to any one of the two ends of the segment 12. For example, a 12 bp long identifier 16 is split to a first 6 bp identifier 16 part and a second 6 bp identifier 16 part. The first identifier 16 part is attached to one end of the segment 12 and the second identifier 16 part is attached to another end of the segment 12.

The unit 1 further comprises an introducer 18 at the 5'-end of the unit 1 and a closure 19 at the 3'-end of the unit 1. According to the embodiment illustrated in FIG. 1A, the introducer 18 is attached to the 5'-end of the index 14 and the closure 19 is attached to the 3'-end of the identifier 16. According to the embodiment illustrated in FIG. 1B, the introducer 18 is attached to the 5'-end of the identifier 16 and the closure 19 is attached to the 3'-end of the index 14.

The introducer 18 and the closure 19 are configured to serve as target sequences for the annealing of primers of a PCR. For example, the introducer 18 is configured to anneal with a forward primer and the closure 19 is configured to anneal with a reverse primer, and vice versa, during PCR cycling. In addition, in a method described hereinafter, sequences of units 1 sequentially attached one to the other are analyzed. Since the introducer 18 and closure 19 are placed at the ends of the unit 1, they are also configured to indicate the borders of the unit 1 sequences.

Segments 12 may be obtained by any method and mechanism known in the art. According to one embodiment, segments 12 may be obtained by shearing of nucleic acids, for example shearing of genomic DNA, total RNA, mRNA and the like. Any type of nucleic acids shearing known in the art is under the scope of the present subject matter. According to this embodiment, for preparing the unit 1, the index 14, identifier 16, introducer 18 and closure 19 are attached to the segments 12 by any method known in the art, for example by ligating them to the segments 12 to obtain the embodiments of the unit 1 illustrated in FIGS. 1A-B. This ligation gives rise to a pre-mature unit 1.

According to another embodiment, segments 12 may be obtained by a first PCR, using forward and reverse primers that define the desired sequence of the segment 12. Thus, the forward primer for the first PCR is specific to a sequence at the 5'-end of the segment 12 and a reverse primer for the first PCR is specific to a sequence at the 3'-end of the segment 12. The template for the first PCR may be any template known in the art that may be a source of segments 12, for example genomic DNA, cDNA library and the like.

According to one embodiment, after the segments 12 are amplified by the first PCR, units are prepared by attaching the index 14, identifier 16, introducer 18 and closure 19 to the amplified segments 12 by any method known in the art, for example by ligating them to the amplified segments 12 to obtain the embodiments of the unit 1 illustrated in FIGS. 1A-B. This ligation gives rise to a pre-mature unit 1.

According to another embodiment, the pre-mature unit 1 may be prepared during the first PCR. According to this embodiment, the primers that are used for amplifying the segments 12 comprise tails with sequences of the index 14, identifier 16, introducer 18 and closure 19.

Figure 2B:
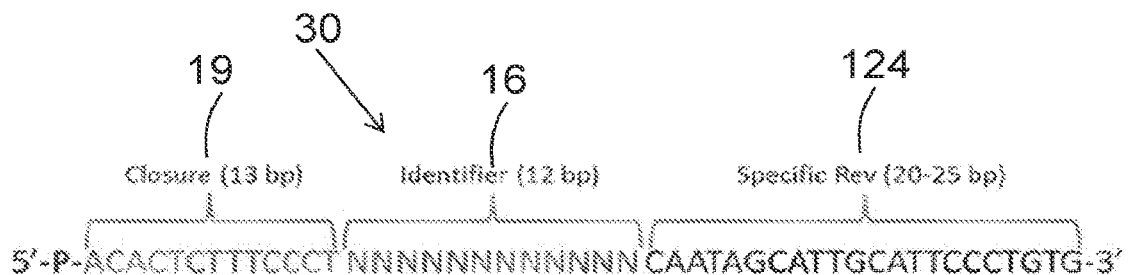

FIGS. 2A-B schematically illustrate, according to an exemplary embodiment, a forward primer and a reverse primer, respectively, for a first PCR. The forward primer 20 for the first PCR, illustrated in FIG. 2A, comprises a specific Fwd 122 sequence CCCTAGTGTGGTAACCTCATTC (SEQ ID NO:8) specific to the 5'-end of the segment 12, an index 14 sequences tail CGTGATCGTGAT (SEQ ID NO:3) attached to the 5'-end of the specific Fwd 122 sequence CCCTAGTGTGGTAACCTCATTC (SEQ ID NO:8) and an introducer 18, that may be termed also introducing 18, sequence tail TGCTCTTCCGATC (SEQ ID NO:9) attached to the 5'-end of the index 14 sequence. The reverse primer 30 for the first PCR, illustrated in FIG. 2B, comprises a specific Rev 124 sequence CAATAGCATTGCATTCCCTGTG (SEQ ID NO:10), specific to the 3'-end of the segment 12 an identifier 16 sequence tail attached to the 3'-end of the specific Rev 124 sequence CAATAGCATTGCATTCCCTGTG (SEQ ID NO:10), and a closure 19 sequence tail ACACTCTTTCCT (SEQ ID NO:11) attached to the 3'-end of the identifier 16 sequence. A person skilled in the art may recognize that the primers illustrated in FIGS. 2A-B give rise, following the first PCR, to the embodiment of the unit 1 illustrated in FIG. 1A. In order to obtain the embodiment of the unit 1 illustrated in FIG. 1B, the primers for the first PCR should be arranged accordingly.

It is designated in FIGS. 2A-B that the range of length of the specific Fwd 122 sequence and the specific Rev 124 sequence is in the range of substantially 20-25 bp. It should be noted that this range of length of the specific Fwd 122 sequence and the specific Rev 124 sequence is only exemplary, and that any length of the specific Fwd 122 sequence and the specific Rev 124 sequence is under the scope of the present subject matter. Similarly, it should be noted that the sequences of the index 14, introducer 18 and closure 19, shown in FIGS. 2A-B, are only exemplary, and that the index 14, introducer 18 and closure 19, as well as the identifier 16, may have any possible sequence in any possible length.

According to one embodiment, the first PCR comprises a low number of amplification cycles, in order to avoid introduction of false mutations in the segment 12 due to poor proofreading by the DNA polymerase used in the PCR. Any number of cycles of the first PCR that produce a sufficient amount of amplicons, namely pre-mature units 1, to be used as templates for a second PCR in one hand, while minimizing the amount of false mutations introduced by DNA polymerase on the other hand, is under the scope of the present subject matter. An exemplary number of cycles of the first PCR is substantially 3-5 cycles.

The pre-mature unit 1 that was made by any way known in the art, for example according to the aforementioned embodiments—nucleic acids shearing and ligation, first PCR and ligation and first PCR, serves as a template for a second PCR.

According to one embodiment, the forward primer used in the second PCR is specific to the introducer 18 and the reverse primer used in the second PCR is specific to the closure 19. It should be noted that the forward and reverse primers of the second PCR do not comprise the index 14 and identifier 16 sequences. As a result, the sequences of the index 14 and identifier 16 are amplified by the DNA polymerase used in the second PCR. Thus, the second PCR is configured to amplify the pre-mature unit 1. The product of the second PCR is a mature unit 1.

According to one embodiment, the mature unit 1, like the pre-mature unit 1, is a double-stranded DNA. The 5'-end of each strand of the mature unit 1 is phosphorylated. Any method for phosphorylating the 5'-ends of the strands of the mature unit 1 is under the scope of the present subject matter. For example, the 5'-ends of the product of the second PCR may be phosphorylated with an enzyme configured to add a phosphate group to a 5'-end of a DNA strand. Another example is to use primers of the second PCR that are phosphorylated at their 5'-ends.

The DNA construct that allows sequencing of short DNA segments, for example in the range of substantially 200-300 bp, by platforms configured to sequence long DNA fragments, in the range of substantially 1,000-10,000 bp, for example the nanopore sequencing platform, is prepared by ligating mature units 1 one to the other, giving rise to a long DNA fragment, in the range of substantially 1,000-10,000 bp.

Figure 3:
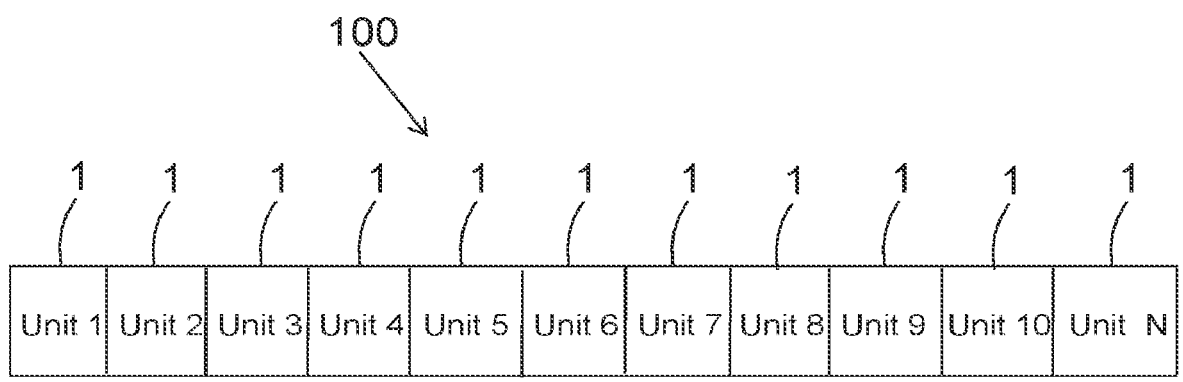
FIG. 3 schematically illustrates, according to an exemplary embodiment, a DNA construct that allows sequencing of short DNA segments.

FIG. 3 schematically illustrates, according to an exemplary embodiment, a DNA construct that allows sequencing of short DNA segments. This DNA construct is designated hereinafter "DNA construct 100". The DNA construct 100 comprises multiple units 1 sequentially attached one to the other. The units 1 may be in any direction one relative to the other. The length of the DNA construct 100 is a length suitable for sequencing by sequencing methods configured to sequence long DNA sequences, for example nanopore sequencing. Thus, for example, the length of the DNA construct 100 may be in the range of substantially 1,000-10,000 bp, and even up to substantially 100,000 bp and more. The units 1 may be sequentially attached one to the other by any method known in the art, for example ligation.

The DNA construct 100 is then sequenced by any method known in the art for sequencing long DNA fragments, for example in the range of substantially 1,000-10,000 bp, and even up to substantially 100,000 bp and more, like nanopore sequencing, and more particularly Oxford Nanopore Technology. The result of this is a nucleotide sequence of the entire DNA construct 100. Any step of the sequencing method until the obtaining of the nucleotide sequence of the DNA construct 100 is under the scope of the present subject matter. This may include for example base calling of the sequences, namely conversion of raw data from the sequencing instrument to nucleotide sequences. This may also include data cleanup, namely trimming of corrupted sequences and sequences that are not related to the sequence of the DNA construct 100, for example very low quality sequences, or sequence element that belong to the sequencing procedure, for example adaptors that are part of the nanopore sequencing method.

The present subject matter provides a method for analyzing a sequence of the DNA construct 100, which as described above may be obtained by any method known in the art. The method for analyzing a sequence of the DNA construct 1 comprises:

separating sequences of units 1 one from the other. This is done by identifying sequences of the ends of the units 1 and separating them in between;

grouping units 1 having the same index 14 for obtaining same index 14 groups. In other words, at this stage the units 1 are classified according to the origins of the target sequences. For example, sequences of one individual are grouped together because they have the same index 14, while sequences of another individual are grouped separately because they have another index 14;

grouping units 1 having the same segment 12 sequence in each same index 14 group, for obtaining same segment 12 group. At the stage, the units 1 of each origin, for example individual, are grouped in separate groups of target DNA, for example separate genes. This is achieved by grouping units 1 having the same segment sequence in one group;

grouping units 1 having the same identifier 16 sequence in each same segment 12 group for obtaining same identifier 16 groups. At this stage, units 1 obtained from the same copy of segment are grouped in one group. As described above, the pre-mature units comprise various copies of a certain target sequence, namely a certain segment 12. Each copy is tagged with a different identifier 16, and then the tagged pre-mature units 1 are amplified in the second PCR for obtaining mature units 1. Thus, each copy of the target sequence, namely the segment 12, is amplified during the second PCR, and errors may be introduced into the segment 12 during amplification. In addition, during the sequencing, errors in reading of the sequence of the segment 12 may be obtained. Therefore, this stage of grouping units 1 having the same identifier 16 sequence is important since it allows identifying errors in the segment 12 sequence due to the procedure and eliminate them, while identifying mutations in the target sequence that are sought for diagnostic purposes. It is easy to distinguish between errors in the segment 12 sequence due to the procedure and mutations in the target sequence, because mutations in the target sequence are detected in all segments 12 tagged with the same identifier 16, while errors due to the procedure may be detected only in one or few segments tagged with the same identifier 16.

Thus, after grouping units 1 having the same identifier 16 sequence in each same segment 12 group, the next step is; collapsing multiple segment 12 sequences in each same identifier 16 group to a single sequence that accurately represents the sequence of the target sequence according to which the segment was obtained. During the collapsing, errors in the sequence due to the procedure are eliminated as described above.

According to one embodiment, the method for analyzing a sequence of the DNA construct 100 further comprises after collapsing multiple segment 12 sequences in each same identifier 16 group to a single sequence—comparing the sequences obtained by the collapsing with known sequences of the target sequences, in order to identify variants in the collapsed sequences of the target sequences (segments 12) compared to the known sequences of the target sequences.

According to another embodiment, the method for analyzing a sequence of the DNA construct 100 further comprises after comparing the sequences obtained by the collapsing with known sequences of the target sequences—reporting mutations found in the variants.

The present subject matter provides a method for preparing the DNA construct 100 described above, the method comprising:
  obtaining a segment 12;
  attaching an index 14, an identifier 16, an introducer 18 and a closure 19 to the segment 12, wherein
  the index 14 is attached to one end of the segment 12;
  the identifier 16 is attached to another end of the segment 12;
  the introducer 18 is attached to a 5'-end of either the index 14 or the identifier 16; and
  the closure 19 is attached to a 3'-end of a remaining either identifier 16 or index 14,
  giving rise to a pre-mature unit 1;
  amplifying the pre-mature unit with primers specific to the introducer and closure, giving rise to a double stranded mature unit 1;
  phosphorylating 5'-ends of the strands of the mature unit 1, and
  sequentially attaching mature units.

Embodiments of the unit 1 are illustrated in FIGS. 1A-B and an embodiment of the DNA construct 100 is illustrated in FIG. 3.

According to one embodiment, the obtaining of the segment 12 is by shearing of a poly-nucleic acid.

According to another embodiment, the poly-nucleic acid is a genomic DNA.

According to yet another embodiment, the poly-nucleic acid is total RNA.

According to still another embodiment, the poly-nucleic acid is mRNA.

According to one embodiment, the obtaining of the segment 12 is by amplifying the segment with primers specific to the segment 12.

According to one embodiment, the attaching of the index 14, identifier 16, introducer 18 and a closure 19 to the segment 12 is by attaching the index 14, identifier 16, introducer 18 and a closure 19 to the primers specific to the segment 12 and amplifying the segment, wherein the index 14 is attached to a 5'-end of either a forward or reverse segment 12 specific primer, the identifier 16 is attached to a 5'-end of a remaining either reverse or forward segment 12 specific primer, the introducer 18 is attached to a 5'-end of either the index 14 or identifier 16 and the closure 19 is attached to a 3'-end of a remaining either identifier 16 or index 14.

Embodiments of the primers to which the index 14, identifier 16, introducer 18 and a closure 19 are illustrated in FIGS. 2A-B.

EXAMPLES

Primers for First PCR

For each mutation to be tested—specific sequences are located for primers that allow amplification of a certain target sequence, also termed "segment", while the primers for the first PCR harbor a desired tested location. Amplicon size is for example substantially 200-400 bp long, the melting temperature (Tm) of the primers is substantially 63-65° C. and the primers length is substantially 18-26 bp. An example for specific primers (forward and reverse) to the BRAF mutation at amino acid position V600:

```
Fwd
                                           (SEQ ID NO: 1)
AGCCTCAATTCTTACCATCCAC,

Rev
                                           (SEQ ID NO: 2)
CTTCATAATGCTTGCTCTGATAGG.
```

For each mutation specific sequence of the first stage primers he following unique elements are added.

```
Index:
                                           (SEQ ID NO: 3)
(12 bases) 5' to the forward specific sequence (example-CGTGATCGTGAT).

Introducer:
                                           (SEQ ID NO: 4)
Addition of 24 bases upstream to the Index (forward primer example-CAAGCAGAAGACGGCATACGAGAT).
```

The length and sequence of the Introducer can vary according to the External-Fwd primer sequence.
Identifier: 12 random bases (12×N) at the 5' end of the reverse specific primer.

```
Closure:
                                           (SEQ ID NO; 5)
Addition of 21 bases upstream to the identifier (reverse primer-AATGATACGGCGACCACCGAG).
```

The length of the Closure and the sequence itself can vary according to the Rev primer sequence.

Primers for Second PCR

Primers for the second PCR are designed to work on every first PCR amplicon. The primers comprise:
A Forward primer having a sequence of the Introducer. The Forward primer may comprise a 5'-Phosphate group, and two phosphorothioate (PS) bonds between the three 3' bases. A Reverse primer having a sequence of the Closure. The Reverse primer may comprise a 5'-Phosphate group, and two phosphorothioate (PS) bond between the $1^{st}$ to $2^{nd}$ and $2^{nd}$ to $3^{rd}$ 3' bases.

First PCR and Second PCR

The procedure comprises a first PCR and a second PCR reaction, each PCR with unique primers as described above. The first PCR is aimed at preparing the target region for the second PCR. The second PCR amplifies only amplicons produced during the first PCR.

First PCR

The following components are added to a sterile strip tube:

| component | µl |
|---|---|
| PCR Master Mix | 12.5 |
| First stage Primer-Fwd (0.1 nM) | 1 |
| First stage Primer-Rev (0.1 nM) | 1 |
| DNA (1-50 ngr) | 1-9.5 |
| Nuclease-free water | Up to 25 |

Set a 50 µl or 100 µl pipette to 20 µl and then pipette the entire volume up and down at least 10 times to mix thoroughly. Perform a quick spin to collect all liquid from the sides of the tube. Place the tube on a thermocycler and perform PCR amplification using the following PCR cycling conditions:

TABLE 1

| Cycle Step | Temp. °C. | Time | Cycles |
|---|---|---|---|
| Initial Denaturation | 95 | 15 minutes | 1 |
| Denaturation | 94 | 30 seconds | 3-5 |
| Annealing | 65 | | |
| Extension | 72 | | |
| Hold for second stage | 10 | ∞ | 1 |
| Denaturation | 94 | 30 seconds | 20-35 |
| Annealing | 65 | | |
| Extension | 72 | | |
| Final Extension | 72 | 5 minutes | 1 |
| Hold | 4 | ∞ | 1 |

PCR program may be changed and adjusted according to the Polymerase enzyme used.

Second PCR

When the first PCR program holds at 10° C., carefully add the second PCR primers (1 µl, 5-10 µM from each primer) and let the PCR program continue.

Clean-Up of PCR Reaction

PCR products from previous step are cleaned for further reactions with AMPure XP magnetic beads (Beckman Coulter).

While using AMPure XP Beads, allow the beads to warm to room temperature for at least 30 minutes before use and vortex the beads firmly to resuspend. Use the AMPure XP Beads for best practice or manufacturer protocol for >250 bp size selection:

Add substantially 0.4× (for 25 µl PCR reaction use 10 µl of resuspended beads) to the PCR reaction. Mix well by pipetting up and down at least 10 times.

Incubate samples on bench top for at least 5 minutes at room temperature.

Place the tube/plate on an appropriate magnetic stand to separate the beads from the supernatant.

After 5 minutes (or when the solution is clear), carefully remove and discard the supernatant. Add 200 µl of 80% freshly prepared ethanol to the tube/plate while in the magnetic stand. Incubate at room temperature for 30 seconds, and then carefully remove and discard the supernatant. Repeat this step for a second ethanol wash. Be sure to remove all visible liquid after the second wash.

Air dry the beads for up to 5 minutes while the tube/plate is on the magnetic stand with the lid open.

Remove the tube/plate from the magnetic stand. Elute the DNA from the beads into 15 µl of Nuclease-free water.

Mix well on a vortex mixer or by pipetting up and down 10 times. Incubate for at least 2 minutes at room temperature. Place the tube/plate on a magnetic stand. After 5 minutes (or when the solution is clear), transfer 13-15 µl to a new PCR tube.

Measure dsDNA in the tube by using Qubit NanoDrop (or equivalent).

Combine equivalent amounts of PCR amplicons/Fragment-Construct from the different panel-PCR tubes.

Amplicon Ligation

Use T4 DNA Ligase (M0202, NEB).

Set up the following reaction in a microcentrifuge tube on ice.

| COMPONENT | 50 µl REACTION |
|---|---|
| T4 DNA Ligase Buffer (10×)* | 5 µl |
| Fragment-Construct DNA | 0.1-0.5 pmol |
| Nuclease-free water | to 50 µl |
| T4 DNA Ligase | 2.5 µl |

*The T4 DNA Ligase Buffer should be thawed and resuspended at room temperature.
**T4 DNA Ligase should be added last.

Gently mix the reaction by pipetting up and down and microfuge briefly.

Incubate at room temperature for 2 hours.

Heat inactivate at 65° C. for 10 minutes.

Chill on ice.

Cleanup of Ligation Reaction

Ligation products from previous step are cleaned for further reactions with AMPure XP magnetic beads (Beckman Coulter).

While using AMPure XP Beads (Beckman Coulter), allow the beads to warm to room temperature for at least 30 minutes before use and vortex the beads firmly to resuspend. Use the AMPure XP Beads for best practice or manufacturer protocol for >250 bp size selection: Add ~0.1X (for 50 µl PCR reaction use 5 µl of resuspended beads) to the PCR reaction. Mix well by pipetting up and down at least 10 times.

Incubate samples on bench top for at least 5 minutes at room temperature.

Place the tube/plate on an appropriate magnetic stand to separate the beads from the supernatant.

After 5 minutes (or when the solution is clear), carefully remove and discard the supernatant. Add 200 µl of 80% freshly prepared ethanol to the tube/plate while in the magnetic stand. Incubate at room temperature for 30 seconds, and then carefully remove and discard the supernatant. Repeat this step for a second ethanol wash. Be sure to remove all visible liquid after the second wash.

Air dry the beads for up to 5 minutes while the tube/plate is on the magnetic stand with the lid open.

Remove the tube/plate from the magnetic stand. Elute the DNA from the beads into 20 µl of 10 mM Tris-HCl or 0.1X TE.

Mix well on a vortex mixer or by pipetting up and down 10 times. Incubate for at least 2 minutes at room temperature. Place the tube/plate on a magnetic stand. After 5 minutes (or when the solution is clear), transfer 17-20 µl to a new PCR tube.

Measure dsDNA in the tube by using Qubit NanoDrop (or equivalent).

Combine equivalent amounts of PCR amplicons/Fragment-Construct from the different panel-PCR tubes.

Preparation of Library and Sequencing with Oxford Nanopore Technologies

Follow one of the protocols for library preparation:
Rapid Sequencing Kit, SQK-RAD004; or
Ligation Sequencing Kit 1D, SQK-LSK108.
Sequence the library by using Oxford Nanopore Technologies platform (MinION, GridION) according to manufacturer's protocol.

Data Analysis

Data analysis is preferably conducted by bioinformatic techniques, and includes the steps mentioned above.

An Alternative Method for Preparing of Mature Units

Previously, mature units were prepared for ligation by a first PCR and a second PCR, when the primers for the first PCR included the introducer, index, identifier and closure sequences. Here described is an alternative method for preparing mature units for ligation.

Conjugating Indices and Identifiers by Ligation
Conjugating UMI's by Ligation

At this stage specific panel at the target genome is amplified in a PCR reaction, while amplified amplicons aren't tagged with indices and identifiers. After the first PCR reaction indices and identifiers as well as introducers and closures are attached by ligation to the amplicons and a second PCR reaction is made in order to amplify the unit. At This stage the first reaction primer are specific primers for a desired location/panel to be sequenced later and do not comprise any elements at their 5'-ends.

This protocol uses the following reagents as a recommendation but can be replaced by alternative reagents/compounds:
1. NEBNext® Ultra™ End Repair/dA-Tailing Module (NEB #E7442).
2. NEBNext® Ultra Ligation Module (NEB #E7445).
3. xGen® Dual Index UMI Adapters.

In general, the procedure comprises the following:
PCR amplification of target regions;
ligation of adaptors with UMI's;
amplification of ligated fragments with secondary primers (primers are designed to be hybridize to the 5' element of the adaptor);
ligation of fragments in order to make long DNA strands of conjugated Fragment-Constructs;
library preparation for long DNA fragments;
data analysis;
mutation report.

First PCR—Amplification of Desired Target Sequence

Preform PCR reaction with high fidelity polymerase enzyme and limited number of cycles (5-15 according to the amount of starting material). Use the target specific primers.

Cleanup of PCR Reaction (Recommended)

PCR products from the first PCR are cleaned for further reactions with AMPure XP magnetic beads (Beckman Coulter) or any other PCR cleanup protocol in order to eliminate residual elements from previous stage such as primers and buffers.

End Repair/dA-Tailing

Follow the NEBNext® Ultra™ End Repair/dA-Tailing Module (NEB #E7442) protocol:
Mix the following components in a sterile, nuclease-free tube:
(green) End Prep Enzyme Mix—3.0 µl;
(green) End Repair Reaction Buffer (10×)—6.5 µl;
PCR amplicons from previous step—55.5 µl;
Mix by pipetting, followed by a quick spin to collect all liquid from the sides of the tube.

Place in a thermocycler, with the heated lid on, and run the following program:
30 minutes @ 20° C.;
30 minutes @ 65° C.;
Hold at 4° C.
Proceed directly to NEBNext Ultra Ligation Module (NEB #E7445):
If DNA input prior to End Repair is <100 ng, dilute the xGen® Dual Index UMI Adapters 1:10 in 10 mM Tris-HCl pH 7.5-8.0 or 10 mM Tris-HCl pH 7.5-8.0 with 10 mM NaCl to a final concentration of 1.5 µM. Use immediately.
Add the following components directly to the End Prep reaction mixture and mix well:
(red) Blunt/TA Ligase Master Mix—15 µl;
xGen® Dual Index UMI Adapters—2.5 µl;
(red) Ligation Enhancer—1 µl.
Mix by pipetting, followed by a quick spin to collect all liquid from the sides of the tube.
Incubate at 20° C. for 15 minutes in a thermocycler.
DNA is now ready for size selection or clean-up.

Cleanup of PCR Reaction (Recommended)

PCR products from previous step are cleaned for further reactions with AMPure XP magnetic beads (Beckman Coulter) or any other PCR cleanup protocol in order to eliminate residual elements from previous stage such as primers and buffers.

Second PCR

This stage amplifies the entire unit from previous stage with primers that hybridize to the exterior elements in the construct (if using xGen® Dual Index UMI Adapters the exterior elements will be the P5 and P7 regions). The primers will have 5' phosphate group for further application.

Preform the second PCR with high fidelity polymerase enzyme and limited number of cycles (5-15 according to the amount of starting material). Use the general amplification primers. If using xGen® Dual Index UMI Adapters use the following primers:

```
                                          (SEQ ID NO: 6)
        /Phos/CAAGCAGAAGACGGCATACGA,
        and (SEQ ID NO; 7)
        /Phos/AATGATACGGCGACCACCGA).
```

Cleanup of PCR Reaction (Recommended)

Products of the second PCR are cleaned for further reactions with AMPure XP magnetic beads (Beckman Coulter) or any other PCR cleanup protocol in order to eliminate residual elements from previous stage such as primers and buffers.

The mature units that were obtained are ligated as described above.

One of the purposes of the present subject matter is to distinguish between errors introduced into a desired target sequence during the procedure its preparation for sequencing and the sequencing itself and between mutations in the target sequence that are sought for the purpose of diagnostics for example. They can be distinguished by sequencing multiple copies of the same target sequence, that is present in the segment while being able to identify sequences of copies of the same template, or target sequence. This is achieved by attaching the identifier 16 to the segment 12. As described above, each copy of the segment 12 is tagged with a specific identifier 16 before the second PCR and before the sequencing of the DNA construct 100. Therefore, sequences of the segment 12 that are tagged with the same identifier are considered identical in the sequence of the original DNA target, while any variation in the sequence between them is considered as originating due to error in the second PCR and the sequencing procedure.

Another unique feature of the present subject matter is the sequential attachment of multiple units, tagged with an identifier 16, as described above, to form a long DNA construct 10 that is suitable for sequencing in methods that are configured for sequencing of very long DNA fragment, like nanopore sequencing. The other components of the unit 1 assist in the analysis of the sequences obtained—The introducer 18 and closure 19 assist in finding the borders of the units in the sequence; the index allows identification of the source of the sequence of the segment 12—thus allowing analysis of sample from multiple sources simultaneously, and the sequence of the segment 12 allow identifying the target sequence—thus allowing analysis of multiple target sequences simultaneously.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A DNA construct comprising multiple units sequentially attached one to the other, wherein a unit comprises:
   a segment comprising a target nucleic acid sequence to be sequenced and analyzed;
   an index attached to one end of the segment;
   an identifier attached to another end of the segment;
   an introducer attached to a 5'-end of either the index or the identifier;
   and a closure attached to a 3'-end of a remaining either identifier or index, wherein
   the index is a DNA sequence that is unique to the origin of the segment and the identifier is a DNA sequence that is unique for every copy of the segment.

2. The DNA construct of claim 1, wherein the length of the DNA construct is at least 1,000 bp.

3. The DNA construct of claim 1, wherein the length of the segment is up to 1,000 bp.

4. The DNA construct of claim 1, wherein the length of the segment is in the range of 100-500 bp.

5. A method for preparing the DNA construct of claim 1, the method comprising:
   obtaining a segment;
   attaching an index, an identifier, an introducer and a closure to the segment, wherein
   the index is attached to one end of the segment;
   the identifier is attached to another end of the segment;
   the introducer is attached to a 5'-end of either the index or the identifier;
   and the closure is attached to a 3'-end of a remaining either identifier or index, giving rise to a pre-mature unit; from
   amplifying the pre-mature unit with primers specific to the introducer and closure, giving rise to a double stranded mature unit;
   phosphorylating 5'-ends of the strands of the mature unit; and
   sequentially attaching mature units.

6. A method for analyzing a sequence of a DNA construct according to claim 1, the method comprising:
   sequencing the units in said construct;
   separating sequenced units in said construct from each other;
   grouping units having the same index for obtaining same index groups;
   grouping units having the same segment sequence in each same index group for obtaining same segment groups;
   grouping units having the same identifier sequence in each same segment group for obtaining same identifier groups; and
   collapsing multiple segment sequences in each same identifier group to a single sequence that accurately represents the sequence of the target sequence according to which the segment was obtained.

7. The DNA construct of claim 1, wherein said identifier in addition to being unique for every copy of the segment, identifies copies of the same target DNA sequence in said DNA segment.

8. The method of claim 5, wherein the index is split into two parts, and each part of the index is attached to any one of the two ends of the segment.

9. The method of claim 5, wherein the identifier is split into two parts, and each part of the identifier is attached to any one of the two ends of the segment.

10. The method of claim 5, wherein the introducer and the closure are configured to indicate borders of the unit during analysis of a sequence of the DNA construct.

11. The method of claim 6, further comprising after collapsing multiple segments sequences in each same identifier group to a single sequence; comparing the sequences obtained by the collapsing with known sequences of the target sequences, to identify variants and/or sequencing errors in the collapsed sequences of the target sequences compared to the known sequences of the target sequences.

* * * * *

```
                         SEQUENCE LISTING

<160> NUMBER OF SEQ ID NOS: 11

<210> SEQ ID NO 1
    <211> LENGTH: 22
    <212> TYPE: DNA
    <213> ORGANISM: Artificial Sequence
    <220> FEATURE:
    <223> OTHER INFORMATION: Synthetic: specific primers-Fwd

<400> SEQUENCE: 1
agcctcaatt cttaccatcc ac                                               22

<210> SEQ ID NO 2
    <211> LENGTH: 24
    <212> TYPE: DNA
    <213> ORGANISM: Artificial Sequence
    <220> FEATURE:
    <223> OTHER INFORMATION: Synthetic: specific primers-Rev

<400> SEQUENCE: 2
cttcataatg cttgctctga tagg                                             24

<210> SEQ ID NO 3
    <211> LENGTH: 12
    <212> TYPE: DNA
    <213> ORGANISM: Artificial Sequence
    <220> FEATURE:
    <223> OTHER INFORMATION: Synthetic: forward specific sequence

<400> SEQUENCE: 3
cgtgatcgtg at                                                          12

<210> SEQ ID NO 4
    <211> LENGTH: 24
    <212> TYPE: DNA
    <213> ORGANISM: Artificial Sequence
    <220> FEATURE:
    <223> OTHER INFORMATION: Synthetic: Introducer

<400> SEQUENCE: 4
caagcagaag acggcatacg agat                                             24

<210> SEQ ID NO 5
    <211> LENGTH: 21
    <212> TYPE: DNA
    <213> ORGANISM: Artificial Sequence
    <220> FEATURE:
    <223> OTHER INFORMATION: Synthetic: Identifier
```

```
<400> SEQUENCE: 5
aatgatacgg cgaccaccga g                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic: primer

<400> SEQUENCE: 6
caagcagaag acggcatacg a                                           21

<210> SEQ ID NO 7
<211> LENGTH: 20
<212> TYPE: DNA
<213> ORGANISM: Artificial Sequence
<220> FEATURE:
<223> OTHER INFORMATION: Synthetic: primer

<400> SEQUENCE: 7
aatgatacgg cgaccaccga                                             20

<210> SEQ ID NO 8
<211> LENGTH: 22
<212> TYPE: DNA
<213> ORGANISM: Artificial Sequence
<220> FEATURE:
<223> OTHER INFORMATION: Synthetic: oligonucleotide

<400> SEQUENCE: 8
ccctagtgtg gtaacctcat tc                                          22

<210> SEQ ID NO 9
<211> LENGTH: 13
<212> TYPE: DNA
<213> ORGANISM: Artificial Sequence
<220> FEATURE:
<223> OTHER INFORMATION: Synthetic: oligonucleotide

<400> SEQUENCE: 9
tgctcttccg atc                                                    13

<210> SEQ ID NO 10
<211> LENGTH: 22
<212> TYPE: DNA
<213> ORGANISM: Artificial Sequence
<220> FEATURE:
<223> OTHER INFORMATION: Synthetic: oligonucleotide

<400> SEQUENCE: 10
caatagcatt gcattccctg tg                                          22

<210> SEQ ID NO 11
<211> LENGTH: 12
<212> TYPE: DNA
<213> ORGANISM: Artificial Sequence
<220> FEATURE:
<223> OTHER INFORMATION: Synthetic: oligonucleotide

<400> SEQUENCE: 11
acactctttc ct                                                     12
```